US011884532B2

(12) United States Patent
Braden

(10) Patent No.: US 11,884,532 B2
(45) Date of Patent: *Jan. 30, 2024

(54) METHOD OF INSTALLATION OF A VACUUMED CONTROLLED LEVEL SENSING LIQUID DISPENSING SYSTEM AND USE THEREOF

(71) Applicant: Michael R. Braden, Fayetteville, TX (US)

(72) Inventor: Michael R. Braden, Fayetteville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/703,715

(22) Filed: Mar. 24, 2022

(65) Prior Publication Data

US 2022/0212914 A1 Jul. 7, 2022

Related U.S. Application Data

(63) Continuation of application No. 17/445,451, filed on Aug. 19, 2021, which is a continuation of application
(Continued)

(51) Int. Cl.
*B67D 3/00* (2006.01)
*B65D 81/20* (2006.01)
(Continued)

(52) U.S. Cl.
CPC ......... *B67D 3/0061* (2013.01); *B65D 1/0223* (2013.01); *B65D 81/2038* (2013.01);
(Continued)

(58) Field of Classification Search
CPC .. B67D 3/0061; B67D 3/0093; B67D 3/0077; B67D 3/00; B67D 3/0051; B67D 3/0045; B67D 99/00; B67D 7/06; B67D 7/64; B65D 1/0223; B65D 1/02; B65D 1/023; B65D 1/0246; B65D 81/2038; B65D 81/20;
(Continued)

(56) References Cited

U.S. PATENT DOCUMENTS 3,930,598 A * 1/1976 Slagle .................. B67D 3/00
222/325
2007/0102332 A1* 5/2007 Bommi .............. B01D 21/0024
210/418
(Continued)

*Primary Examiner* — Akash K Varma
(74) *Attorney, Agent, or Firm* — Miguel Villarreal, Jr.; Gunn, Lee & Cave, P.C.

(57) ABSTRACT

A gravity flow liquid disinfectant dispensing reservoir comprised of a tapered base and a neck portion that extends centrally from the reservoir. An aperture located on the bottom of the reservoir facilitates the dispensing of liquid (i.e., disinfectant) from the reservoir into a holding tank. In another embodiment, a closed system for dispensing a liquid disinfectant into a tank containing liquid (effluent) and controlled via vacuum. The gravity flow device introduces disinfectant to the tank as the water level rises, giving the ultimate amount of contact time for treatment of effluent. Utilizing gravity and vacuum controlled dispensing of disinfectant dispenses disinfectant continuously and automatically in real time and provides for maximum contact time for minimal pathogen survival.

2 Claims, 14 Drawing Sheets

Related U.S. Application Data

No. 16/299,111, filed on Mar. 11, 2019, now Pat. No. 11,286,151.

(60) Provisional application No. 62/641,398, filed on Mar. 11, 2018.

(51) Int. Cl.
  *B67D 99/00* (2010.01)
  *B65D 1/02* (2006.01)
  *A61L 2/18* (2006.01)

(52) U.S. Cl.
  CPC ............ *B67D 3/0093* (2013.01); *B67D 99/00* (2013.01); *A61L 2/186* (2013.01); *B67D 3/0077* (2013.01)

(58) Field of Classification Search
  CPC ........ B65D 51/16; B65D 51/20; B65D 47/10; B65D 47/32; B65D 47/06; B65D 47/04; B65D 47/063; B65D 47/043; B65D 47/24; B65D 47/242; B65D 47/2031; B65D 47/12; B65D 47/125; B65D 25/32; B65D 25/46; B65D 25/44; B65D 25/42; B65D 25/465; B65D 2501/0081; B65D 2205/00; B65D 41/0442; B65D 41/0435; B65D 41/04; B65D 41/06; B65D 88/04; B65D 7/04; A61L 2/186; B65B 39/00; G01F 19/00
  USPC .......................................... 210/121; 222/173
  See application file for complete search history.

(56) References Cited

U.S. PATENT DOCUMENTS

2008/0273915 A1* 11/2008 O'Connell .............. A61L 2/186
  222/23
2009/0206106 A1* 8/2009 Perez Ordonez ........ B67D 3/00
  222/129
2017/0079468 A1* 3/2017 Apone .................. A47J 31/467

* cited by examiner

METHOD OF INSTALLATION OF A VACUUMED CONTROLLED LEVEL SENSING LIQUID DISPENSING SYSTEM AND USE THEREOF

CROSS-REFERENCES TO RELATED APPLICATIONS

This is a continuation application claiming priority to and the benefit of U.S. application Ser. No. 17/445,451, filed Aug. 19, 2021, entitled "Vacuumed Controlled Level Sensing Liquid Dispensing System," which claims priority to and the benefit of U.S. application Ser. No. 16/299,111, filed Mar. 11, 2019, which claims priority to and the benefit of U.S. provisional application Ser. No. 62/641,398, filed Mar. 11, 2018, entitled "Vacuumed Controlled Level Sensing Liquid Dispensing Device," all of which are incorporated by reference herein.

STATEMENT REGARDING FEDERALLY-SPONSORED RESEARCH OR DEVELOPMENT

None.

BACKGROUND OF THE INVENTION

1. Field of the Invention

The present invention relates to liquid dispensing devices. More specifically, the invention relates to a system and method for the continuous dispensing of liquid disinfectant whereby such dispensing is controlled by vacuum.

2. Description of the Related Art

There exists in the art devices for dispensing a disinfectant to disinfect fluid or liquid prior to utilization of the disinfected liquid. For example, there are devices for use in connection with septic systems that dispense chlorine into a tank for disinfecting the accumulated liquid prior to dispersion of the disinfected liquid to a sprinkler or drain field. These kinds of systems may either use solid (e.g., tablets) or liquid disinfectants. The disinfectant is further generally drawn or pulled into the liquid to be disinfected using a venturi through a phenomenon known as the venturi effect. The disinfectant used is generally chlorine.

However, there may be certain environments or regulations that do not allow certain types of disinfectants to be used or where a disinfectant other than chlorine is desired. In additional, there may be several components that comprise the disinfecting dispensing equipment which translates to multiple potential areas of failure. This would, in turn, require additional maintenance and increased costs to maintain the equipment. Having more replacement components translates to having to accommodate additional replacement parts in inventory.

Current wastewater treatment systems also impact the environment as the amount of disinfectant used often exceeds the amount needed to effectively treat wastewater. For example, current disinfecting systems using a venturi may release up to 15 drops of liquid (which is equal to 1 mL) in 1 gallon of treated wastewater. In other words, it takes 15 drops of liquid bleach to treat 1 gallon of wastewater.

Accordingly, there is a need for a stand-alone dispensing device that has a free flow gravity feed design that is environmentally friendly, low cost, easily installable on to any aerobic system and contains no moving parts. There is a further need for such device to be vacuum controlled such that the device dispenses disinfectant to a liquid continuously and in real time. There is also a further need for a dispensing device that is capable of dispensing a variety of types of disinfectants in accordance with applicable environmental, regulatory and/or consumer constraints. The present invention addresses these and other shortcomings of the currently existing disinfecting systems.

BRIEF SUMMARY OF THE INVENTION

The present invention provides a closed system for dispensing a liquid disinfectant into a tank containing liquid (effluent) without using a venturi to dispense the disinfectant. Rather, the dispensing of the disinfectant is controlled via a vacuum. The present invention further provides for a gravity flow device that applies disinfectant to a holding tank as the water level rises, thus, giving the ultimate amount of contact time for the disinfectant to work. The disinfectant is introduced to effluent water in a holding/pump tank as the effluent enters the holding/pump tank. The longer the contact time the disinfectant has to interact with pathogens, the better the disinfectant disinfects and treats the effluent water. In short, the present invention provides for maximum contact time for minimal pathogen survival.

The inventor conducted a series of experiments demonstrating the underlying principles supporting the present invention and observed that 1" Hg was sufficient in any size pipe to raise water within such pipe approximately 14" in the pipe. In these experiments, the invention used six different sized pipes—also described as "sensing pipes"—having diameter sizes of 1¼", 1", ¾", ½", ⅜" and ¼". Each was tied together via tubing to a header having a ball valve. The water was dyed to demonstrate visually the effect the vacuum had on the water within the sensing pipe. The header was connected via tubing to a vacuum gauge which was approximately at 0.0" Hg. This then was connected via tubing to a venturi.

When the venturi was turned on (which created a vacuum within the system), the water within each of the sensing pipes rose simultaneously and notably at the same rate with the same amount of vacuum being applied to each sensing pipe of differing diameters. After turning off the venturi, and thus ceasing the application of vacuum, the vacuum sensor measured approximately 1" Hg of vacuum. The ball valve on the header was shut off thus, maintaining the vacuum within the sensing pipe.

What was observed was that the distance the dyed water rose in each of the sensing pipes of different diameters was about 14 inches above the surface of the water. In other words, the column of water within each of the sensing pipes was approximately 14"-15" inches from the water surface. This length of water column within the sensing pipe and above the water surface was maintained consistently so long as the vacuum was maintained. Once the system lost vacuum, the water column began to fall down towards the surface of the water.

In an alternative embodiment, if a T was placed inline and connected to a vacuum switch (e.g., low level), the gauge was normally a closed switch with 0.38" to 1" Hg. As long as the system was under vacuum, the system pulled the switch open. However, a low level functioning alarm was also tied in to indicate when the level was low. When vacuum was lost, the alarm went off.

While this demonstration was prepared using a venturi to create the vacuum, the present invention operates absent a venturi.

An object of the present invention is to control the dispensing of a liquid disinfectant without a venturi.

A further object of the present invention is to provide for a disinfection device for secondary treated effluent.

A still further object of the present invention is to provide for a disinfection device that may be used with 6-10% sodium hypochlorite (household bleach) as the liquid disinfectant.

Yet another object of the present invention is to provide for a disinfection device that may be used with various kinds of disinfectants as the liquid disinfectant.

A further object of the present invention is to provide the maximum amount of contact time between the liquid disinfectant and the liquid to be treated.

To contrast the prior art to the present invention, reference is now made to FIG. 1 which depicts graphical representation 10 illustrating the relationship between the amount of liquid in the tank and the level of residual chlorine as a function of time for front side dosing using a venturi front of pump cycle. Front side dosing means all dose is provided as the pump starts. Left axis 12 represents the quantity of liquid (gal.). Right axis 14 represents the current level of residual chlorine (mg/L). Bottom axis 16 represents time (24 hours). Metered flow is a slow steady addition of chlorine drops when the pump starts and continues to run. However, once the initial dosage is provided, minimal, if any, disinfecting occurs until the pump cycle resumes. In contrast, the present invention, without the use of a venturi, controls the dosage of disinfectant into the tank of effluent to be treated to disinfect continuously and in real time.

Utilizing gravity and vacuum controlled dispensing of disinfectant rather than a venturi to control the dispensing or dosing of the disinfectant, the present invention thus dispenses disinfectant continuously in real time. This may be demonstrated quantitatively. Referring now to FIG. 2, graphical representation 18 illustrates the relationship between the amount of liquid in the tank and the level of residual chlorine as a function of time. Left axis 20 represents the quantity of liquid (gal.). Right axis 22 represents the current level of residual chlorine (mg/L). Bottom axis 24 represents time (24 hours).

As shown in FIG. 2, an almost linear and proportional relationship between the amount of chlorine and water exists as a function of time. At the start of the pump cycle (12 am) the quantity of water in the pump tank is 0.0 gal. and the residual chlorine is near 2.0. Then at 3:00 am, there is an increase of water to about 10 gal. At that time the residual chlorine is at about 1.5. At 6 am, the water level increases to about 50 gal. and the residual chlorine is about 1.0. The residual chlorine level decreases until about 7 am then begins to increase in concentration. At about 9 am the residual chlorine level is about 0.75 whereas the water level has increased to about 100 gal. This proportional increase of both the water level and residual chlorine concentration level continues until about 12 am where the water quickly decreases from about 250 gal. to about 50 gal. while the residual chlorine plateaus at about 2.0. This would then coincide to the residual chlorine level described at the beginning of the pump cycle. The water level also continues to decrease after the pump cycle back down to 0.0 gal. before the next pump cycle begins. As the water level in the tank increases (from between 6 am to 12 am), there appears to be a somewhat linear relationship with the chlorine level which also increases proportionately during this same time period.

Stated differently, at the start of a pump cycle, the water level in the pump/holding tank is high enough, as all of the daily water usage is satisfied by a level float, probably until midday. However, the water held in the tank is monitored by a timer and is not generally satisfied by midnight (timer setting). When both the float level and the timer settings coincide, the pump cycle begins.

Some jurisdictions, e.g., Texas, require spray discharge/pump cycle to occur between 12 am-5 am. It is important to note that there is always about 100-150 gallons or more in the tank all the time at "0" (See FIG. 2) because the pump intake is about 12" off the bottom of the tank. There is always about 16-18" of water in a tank because of the location of the pump intake. The graph starts at 0 which corresponds to daily water usage. Water level/usage decreases overnight due to inactivity, e.g., everyone is sleeping. In the morning the water level and water usage increases, then becomes stagnant and maybe increases during the lunch hour and continues to increase when everyone is at home in the evening using water before bedtime.

When stagnant water flows, chlorine residuals decline due to the nature of agressive/nonstable sodium hypochlorite (bleach). When flows are present, chlorine residuals are proportionally linear. See FIG. 2.

Over the course of several experiments, the inventor discovered that an increase in the inner diameter of the sensing tube translated into an observed increase in the resulting chlorine concentration in the pump tank with no losses of chlorine. For example, with a 500 gal pump tank, using a concentration of sodium hypochlorite of 6.25%, a sensing tube of 0.5 inches in diameter and having the following parameters:

| Pump Tank Wet Well Height | 55 | inches |
| Pump Tank Total Volume | 771 | gallons |
| Unit Volume | 14.02 | gal/inch |
| Sensing Tube Diameter | 0.5 | inches |
| Sodium Hypochlorite Concentrations | 6.25% | |

The following resulted:

TABLE 1

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
| --- | --- | --- | --- | --- | --- | --- | --- |
| 0.5 | 26.53 | 1.61 | 1.61 | 0.0004 | 24 | 55.7 | 2.1 |

When the sensing tube diameter was increased to 0.75 inches, and maintaining the remaining parameters, the results were as follows:

TABLE 2

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 26.53 | 3.62 | 3.62 | 0.0010 | 54 | 125.2 | 4.7 |

Increasing the sensing tube diameter to 1.00 (all other parameters unchanged), gave the following:

TABLE 3

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 26.53 | 6.43 | 6.43 | 0.0017 | 96 | 222.6 | 8.4 |

The inventor performed a similar experiment increasing the sodium hypochlorite concentration to 8.00% but all other parameters remaining unchanged:

| | | |
|---|---|---|
| Pump Tank Wet Well Height | 55 | inches |
| Pump Tank Total Volume | 771 | gallons |
| Unit Volume | 14.02 | gal/inch |
| Sensing Tube Diameter | 0.5 | inches |
| Sodium Hypochlorite Concentrations | 8.00% | |

The following resulted:

TABLE 4

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 26.53 | 1.61 | 1.61 | 0.0004 | 24 | 71.2 | 2.7 |

When the sensing tube diameter was increased to 0.75 inches, and maintaining the remaining parameters, the results were as follows:

TABLE 5

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank w/ no losses (mg/L) |
|---|---|---|---|---|---|---|---|
| 0.5 | 26.53 | 3.62 | 3.62 | 0.0010 | 54 | 160.3 | 6.0 |

Increasing the sensing tube diameter to 1.00 (all other parameters unchanged), gave the following:

TABLE 6

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank w/ no losses (mg/L) |
|---|---|---|---|---|---|---|---|
| 0.5 | 26.53 | 6.43 | 6.43 | 0.0017 | 96 | 285.0 | 10.7 |

The inventor performed a similar experiment increasing the sodium hypochlorite concentration to 10% but all other parameters remaining unchanged:

| | | |
|---|---|---|
| Pump Tank Wet Well Height | 55 | inches |
| Pump Tank Total Volume | 771 | gallons |
| Unit Volume | 14.02 | gal/inch |
| Sensing Tube Diameter | 0.5 | inches |
| Sodium Hypochlorite Concentrations | 10% | |

The following resulted:

TABLE 7

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank w/ no losses (mg/L) |
|---|---|---|---|---|---|---|---|
| 0.5 | 26.53 | 1.61 | 1.61 | 0.0004 | 24 | 89.1 | 3.4 |

When the sensing tube diameter was increased to 0.75 inches, and maintaining the remaining parameters, the results were as follows:

TABLE 8

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 26.53 | 3.62 | 3.62 | 0.0010 | 54 | 200.4 | 7.6 |

Increasing the sensing tube diameter to 1.00 (all other parameters unchanged), gave the following:

TABLE 9

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 26.53 | 6.43 | 6.43 | 0.0017 | 96 | 356.2 | 13.4 |

Increasing the pump tank size produced similar results. For example, with a 1000 gal pump tank, using a sensing tube of 0.5 inches in diameter, and having the following parameters:

| Pump Tank Wet Well Height | 56 | inches |
|---|---|---|
| Pump Tank Total Volume | 1220 | gallons |
| Unit Volume | 21.79 | gal/inch |
| Sensing Tube Diameter | 0.5 | inches |
| Sodium Hypochlorite Concentrations | 6.25% | |

The following resulted:

TABLE 10

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 41.23 | 1.61 | 1.61 | 0.0004 | 24 | 55.7 | 1.4 |

When the sensing tube diameter was increased to 0.75 inches, and maintaining the remaining parameters, the results were as follows:

TABLE 11

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 41.23 | 3.62 | 3.62 | 0.0010 | 54 | 125.2 | 3.0 |

Increasing the sensing tube diameter to 1.00 (all other parameters unchanged), gave the following:

TABLE 12

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 41.23 | 6.43 | 6.43 | 0.0017 | 96 | 222.6 | 5.4 |

Increasing the pump tank size produced similar results. For example, with a 1000 gal pump tank, using a sensing tube of 0.5 inches in diameter, and having the following parameters:

| Pump Tank Wet Well Height | 56 | inches |
|---|---|---|
| Pump Tank Total Volume | 1220 | gallons |
| Unit Volume | 21.79 | gal/inch |
| Sensing Tube Diameter | 0.5 | inches |
| Sodium Hypochlorite Concentrations | 6.25% | |

The following resulted:

TABLE 13

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 41.23 | 1.61 | 1.61 | 0.0004 | 24 | 55.7 | 1.4 |

When the sensing tube diameter was increased to 0.75 inches, and maintaining the remaining parameters, the results were as follows:

TABLE 14

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 26.53 | 3.62 | 3.62 | 0.0010 | 54 | 125.2 | 4.7 |

Increasing the sensing tube diameter to 1.00 (all other parameters unchanged), gave the following:

TABLE 15

| Change in Pump Tank Height (in.) | Equivalent Volume (L) | Sensing Tube Volume Change (mL) | Equivalent Volume Bleach (mL) | Equivalent Volume Bleach (gal.) | Equivalent Volume (drops) | Mass Chlorine Dosed (mg) | Resulting Chlorine Concentration in Pump Tank with no losses (mg/L) |
|---|---|---|---|---|---|---|---|
| 0.5 | 26.53 | 6.43 | 6.43 | 0.0017 | 96 | 222.6 | 8.4 |

As demonstrated above, these calculations demonstrate that varying the diameter of the different sensing tubes directly affects the chlorine dose.

The dispensing system of the present invention adjusts the amount of chlorine that drips into the pump tank by controlling the amount of air allowed into the disinfectant dispensing reservoir via the sensing pipe. A different size will give a different result. The flexible tubing from the top of the sensing pipe connects directly into the liquid dispensing reservoir, preferably at the highest point as it is a "vent," but only in the sense that the reservoir only receives air from the sensing pipe, not atmosphere, as the present invention is a closed system.

As the water column rises, this allows air to enter into the reservoir and by entering into the reservoir, the vacuum within the plastic tubing is lessened which allows the dispensing tube to dispense fluid, e.g., disinfectant, such as chlorine.

The present invention demonstrates that 1" Hg lifts approximately 14" of water column. The column of air above the water column controls the feed rate (chlorine dosage) of the liquid dispensing reservoir. Reducing the diameter of column of air (by reducing the inner diameter of the sensing pipe) reduces the amount of air fed into the air locked liquid dispensing reservoir.

The present invention substantially reduced the amount of disinfectant required to treat wastewater over current disinfecting systems. The present invention reduces the amount of liquid chlorine used by about half. With the present invention, it now only takes 7 drops of bleach per gallon to effectively treat wastewater. This is tantamount to about 16,000 gallons of water treated with about 2 gallons of disinfectant, e.g., bleach. This is quite an unexpected result. The inventor is not aware of any other device or system that can effectively treat this much wastewater with such a minimal amount of liquid chlorine. The benefits of reducing the amount of disinfectant to effectively treat wastewater include a more environmentally friendly treatment system and a reduction on cost for consumables and operating costs.

An advantage of the present invention is the free flow gravity feed design that is easily installable on to any aerobic system and contains no moving parts. An additional advantage is that the present invention is vacuum controlled such that the device dispenses disinfectant to a liquid continuously and in real time. Still another advantage is that the present invention is capable of dispensing a variety of types of disinfectants in accordance with applicable environmental, regulatory and/or consumer constraints while reducing the number of components and consumables which translates into substantial cost savings.

DETAILED DESCRIPTION OF THE INVENTION

Figure 1:
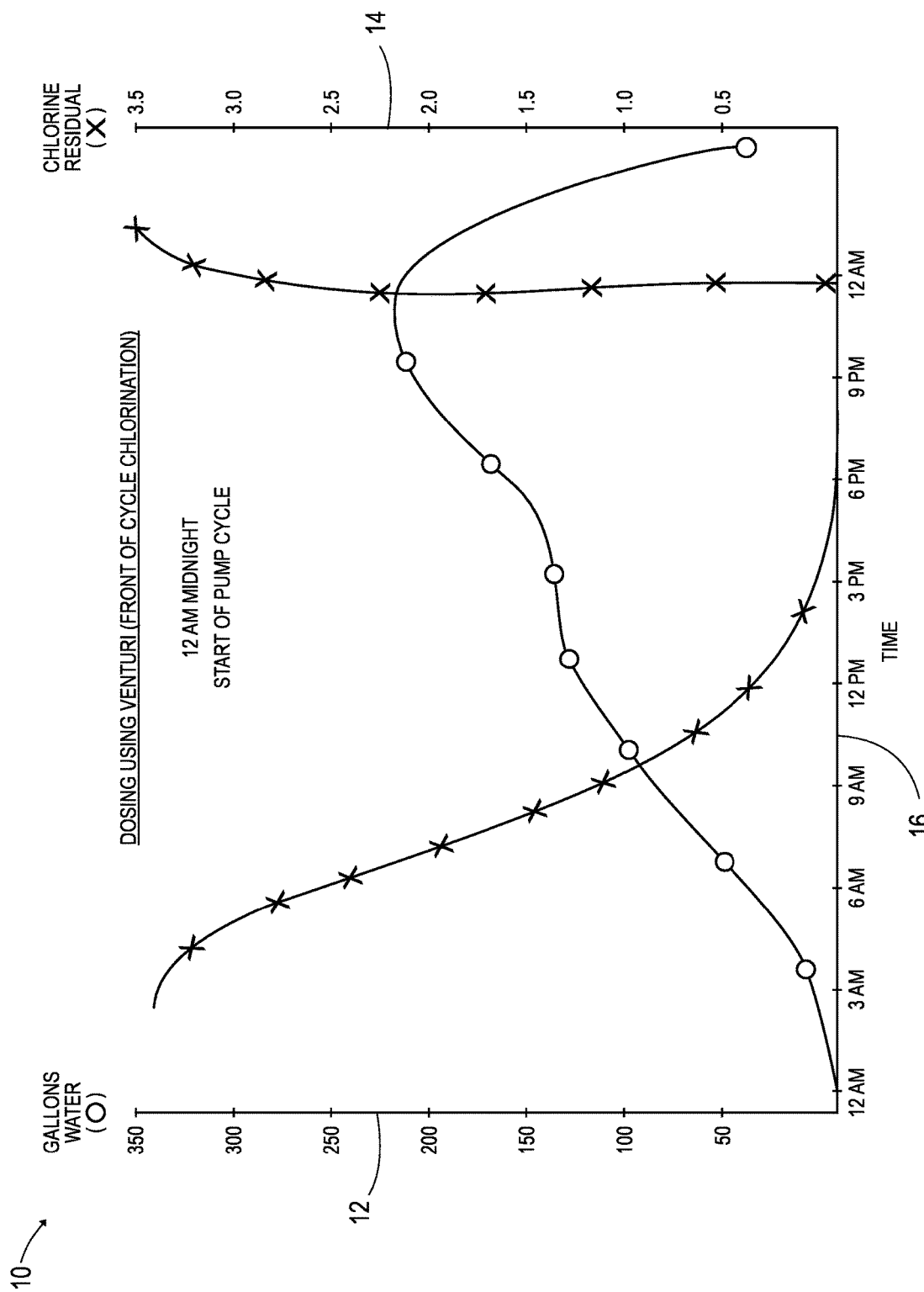
FIG. 1 depicts a graphical representation of the typical monitoring results of an existing dispensing device that utilizes a venturi.
Figure 2:
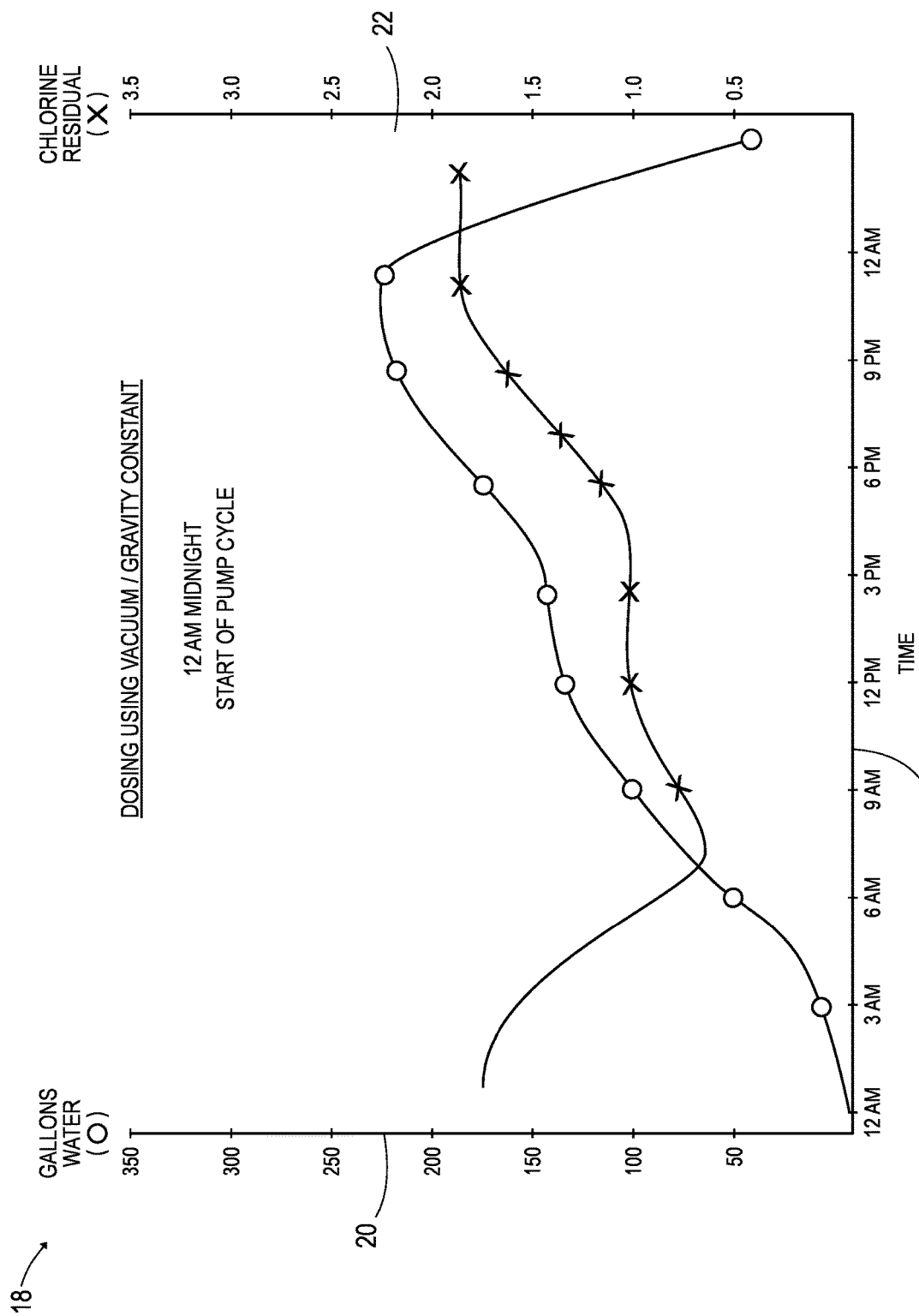
FIG. 2 depicts a graphical representation of the typical monitoring results of the present invention.
Figure 3:
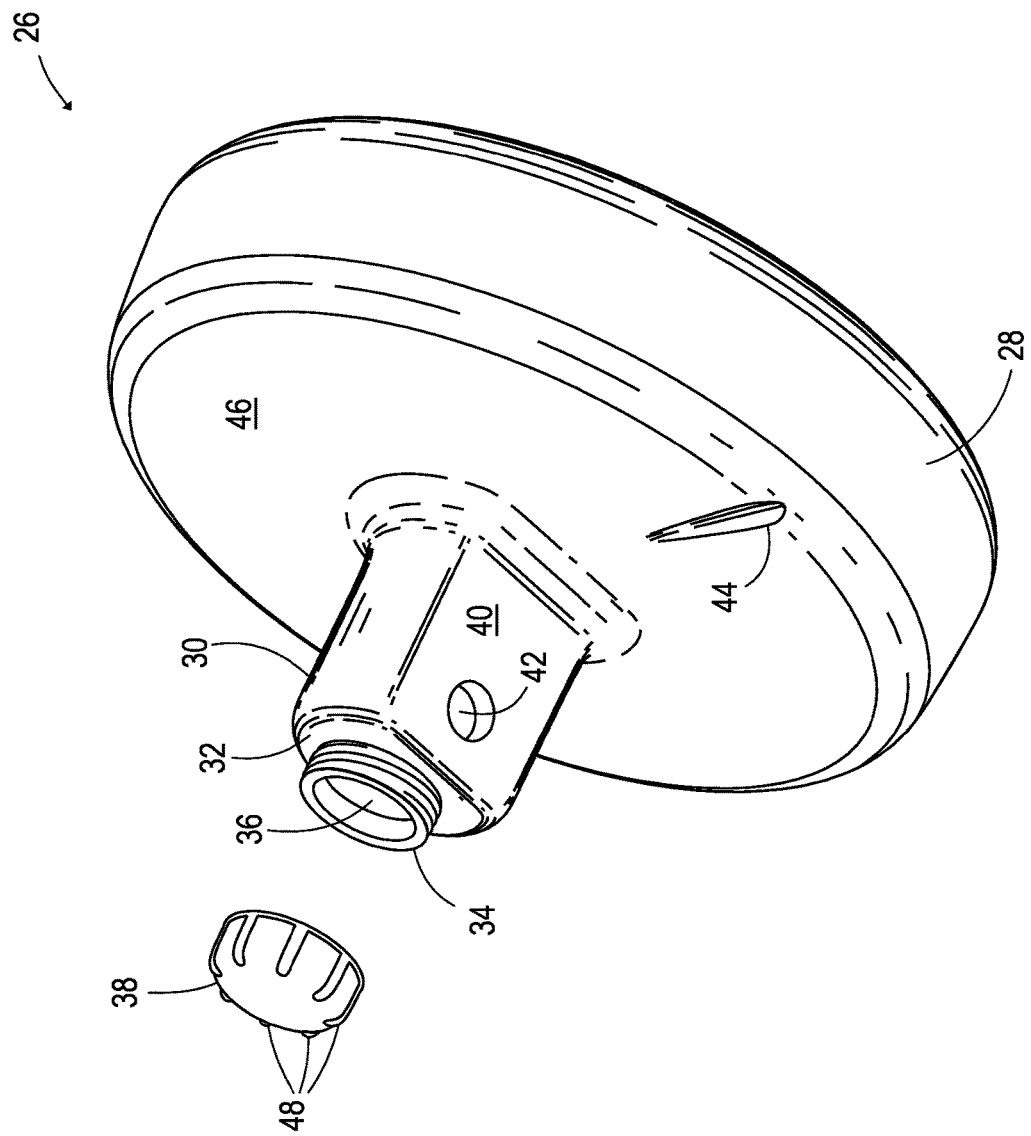
FIG. 3 is a perspective front view of a disinfectant dispensing reservoir of an embodiment of the present invention.

Referring now to FIG. 3, the liquid disinfectant dispensing reservoir of the present invention is shown. The reservoir has a tapered base 28. Neck portion 30 extends centrally from top surface 46 of liquid dispensing reservoir 26. End 32 of neck portion 30 opposite base 28 is tapered and threaded. Threaded portion 34 protrudes from end 32 of neck portion 30. Aperture 36 within threaded portion 34 provides pathway for liquid disinfectant to enter within liquid dispensing reservoir 26.

Aperture 42 on flat portion 40 allows a fitting, such as a barbed fitting, to be secured therein. Aperture 42 and fitting (not shown) may have complimentary threaded portions that engage there between. Alternatively, the fitting may be secured within aperture 42 using a sealant, such as a waterproof sealant. The sealant is not exposed to disinfectant, e.g., chlorine, at any time. The fitting facilitates and allows for connection to the tubing that will (at the other end of the tubing) connect to the sensing pipe (see, e.g., FIG. 8), as will be described in further detail below. The present invention uses a barbed fitting, though other kinds of fittings, connectors or couplings may be used and still remain within the contemplation of the present invention.

Still referring to FIG. 3, releasably attached cap 38 having internal threads (not shown) is matable with the threaded end 34 of neck portion 30 of liquid dispensing reservoir 26. The interior threading of screw cap 38 allows for mating with and threading to protruded threaded portion 34. Screw cap 38 may have ridges 48 or be knurled to facilitate and aid a user to screw the screw cap 38 on and off more easily from protruded threaded portion 34. Screw cap 38 may be made of polyethylene and may also contain a gasket (not shown).

Figure 4:
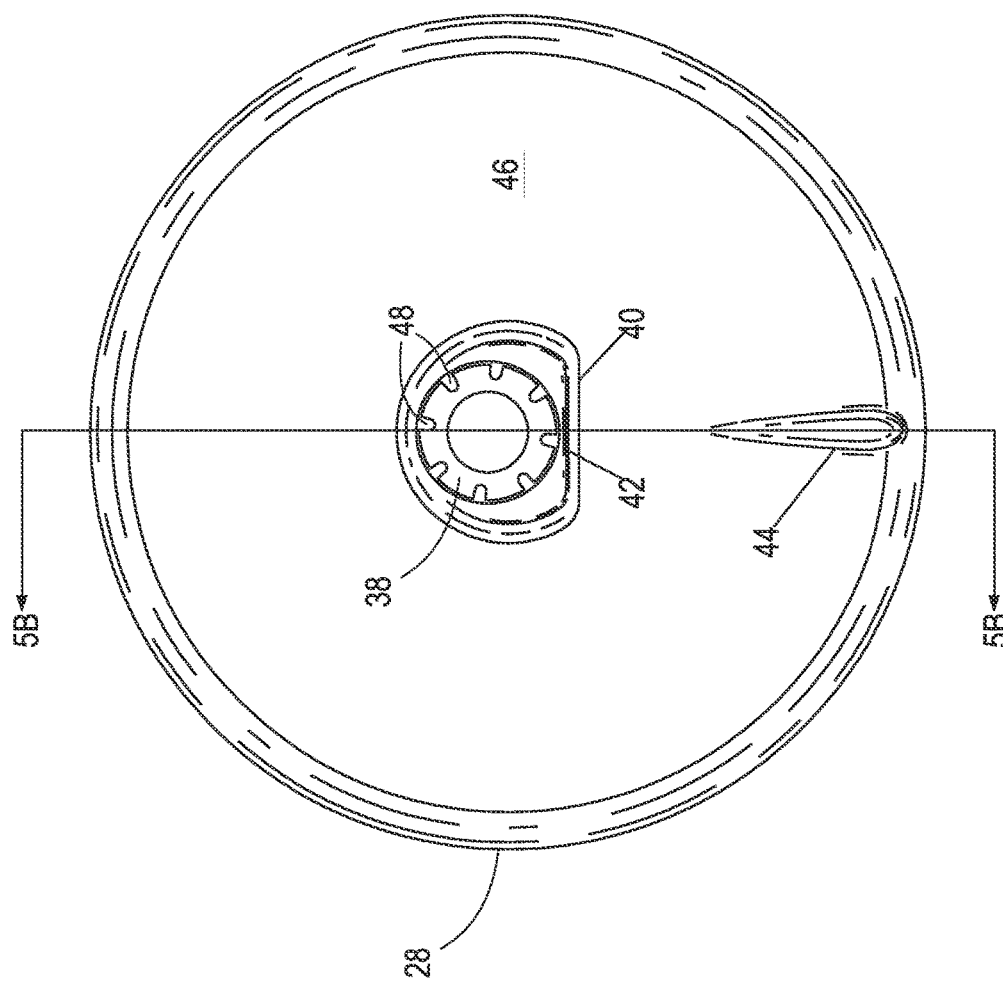
FIG. 4 is a top view of the disinfectant dispensing reservoir of an embodiment of the present invention.

Referring now to FIG. 4, a top view of liquid dispensing reservoir 26 is shown. Partial groove 44 is located on top surface 46 directly in front of aperture 42.

Figure 5:
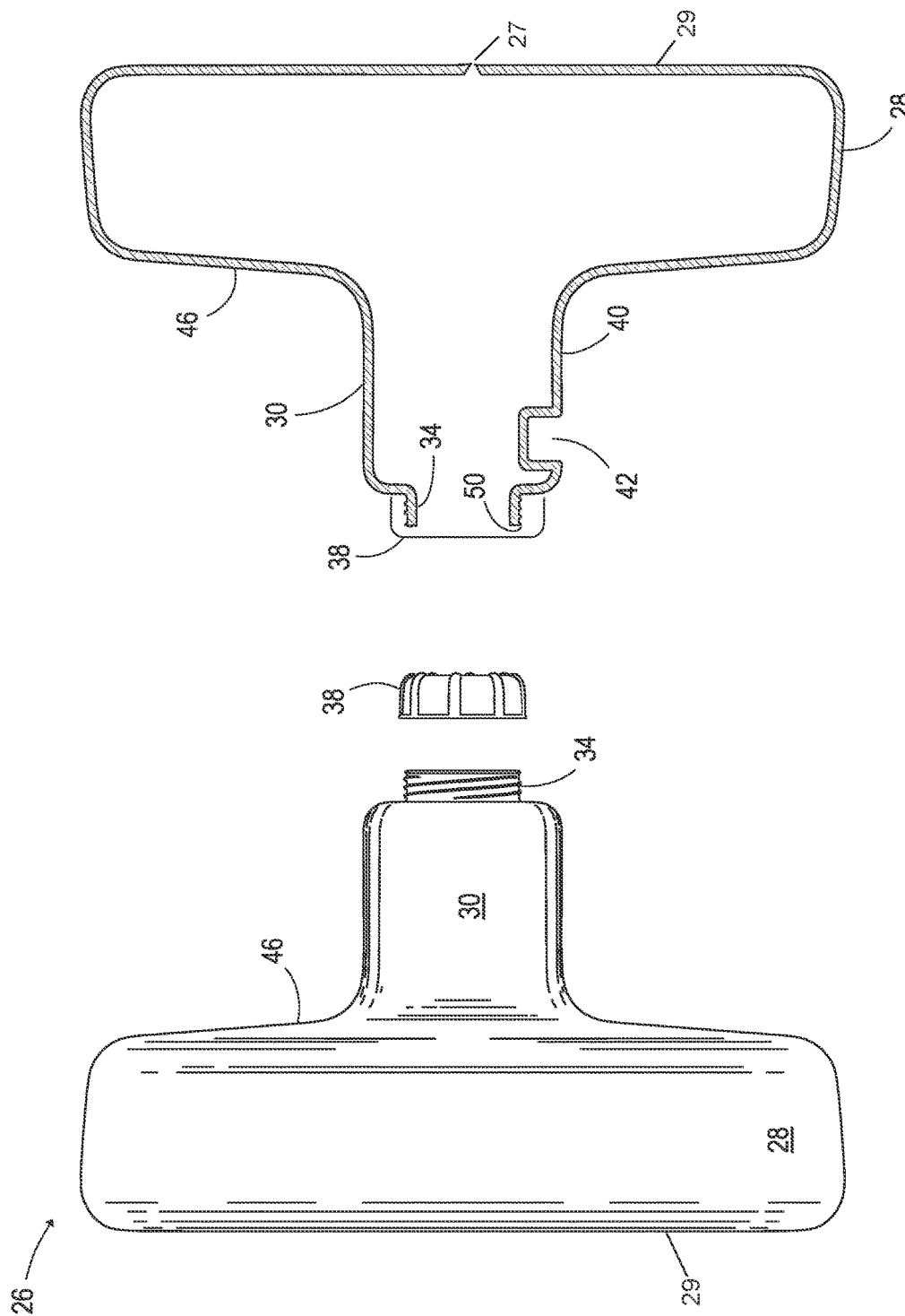
FIG. 5A is a back view of the disinfectant dispensing reservoir of an embodiment of the present invention.
FIG. 5B is a right side cross section view of the disinfectant dispensing reservoir of an embodiment of the present invention taking across section lines 5B with respect to FIG. 4.

Referring now to FIGS. 5A and 5B, a side view and cross sectional view of liquid dispensing reservoir 26 is shown. Base 28 tapers toward top surface 46. Cap 38 releasably attaches to threaded portion 34 of neck portion 30, as shown in FIG. 5A. The cross sectional view in FIG. 5B illustrates internal threads 50 of cap 38 engaged with external threads of threaded portion 34. The volume within liquid dispensing reservoir 26 fills with and holds liquid disinfectant.

Still referring to FIG. 5B, aperture 27 is centrally located on bottom 29 of liquid dispensing reservoir 26. Aperture 27 facilitates the dispensing of liquid (i.e., disinfectant) from liquid dispensing reservoir 26. The size of the aperture on the bottom of liquid dispensing reservoir 26 may vary in size proportionally with the thickness of the material used for liquid dispensing reservoir 26. The thicker the material, the larger the aperture. In the present invention, aperture 27 is 1/8" in diameter though other aperture sizes, ranging from about 1/16" and larger, may be used and still remain within the contemplation of the present invention.

Dimensions for liquid dispensing reservoir 26 include base 28 having a height of 4 inches and a 5 degree taper toward neck portion 30 of the reservoir. Neck portion 30 has a length of 4.50 inches, a 0.25" radius across the middle portion of neck portion 30 and a 0.5" radius at end 32 adjacent to threaded portion 34 of neck portion 30. Offset center of opening 36 is 0.25" from the center of neck portion 30. Flat area 40 on the opposite side of neck portion 30 is 0.75" from centerpoint and forms an approx. 3"×3" flat square area and may be for placement of embossed labeling, logo, data plate or other similar marking. The length of the reservoir from base 28 to threaded portion 34 of neck portion 30 is 8.50 inches. While the present invention has these dimensions, other dimensions may also be used and still remain within the contemplation of the present invention.

The reservoir is constructed from durable polyethylene material which can withstand the corrosive nature of sodium hypochlorite (i.e., household bleach). The cap is a 63 mm polyethylene screw cap with gasket. While the present invention uses polyethylene, any similarly resistant material may also be used and still remain within the contemplation of the present invention.

In one embodiment, during fabrication of liquid dispensing reservoir 26, a 1/8" National Pipe Thread Taper (NPT) pipe plug is inserted in the mold (at the highest point of flat portion 40 of the fill neck portion 30) for liquid dispensing reservoir 26 prior to molding. This plug is a removable/reusable piece that will create the threads needed for the threaded barb elbow or fitting that attaches and connects to tubing for transfer of liquid from liquid dispensing reservoir 26 to another component (sensing pipe), as will be described below. Tubing used in the present invention may be vinyl tubing, though other comparably resistant and flexible material may be used and still remain within the contemplation of the present invention. Liquid dispensing reservoir 26 may be manufactured via rotational molding. However, given cost considerations, it may be preferably manufactured using extrusion blow molding.

Figure 6:
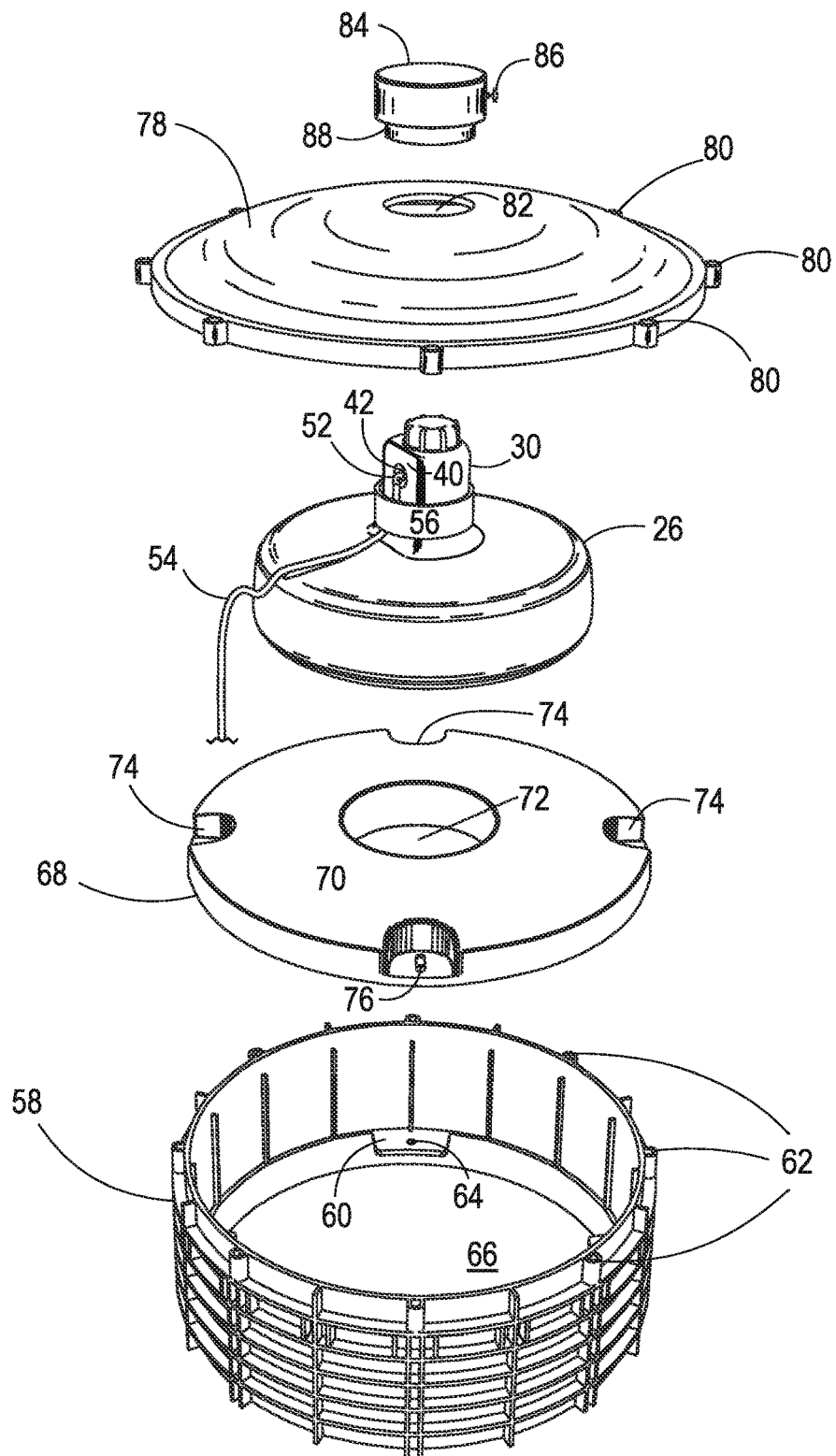
FIG. 6 depicts an exploded view of the disinfectant dispensing reservoir and housing of an embodiment of the present invention.

The liquid dispensing reservoir of the present invention may be incorporated into the dispensing system of the present invention. The dispensing system of the present invention is generally underground. However, the upper portion of the dispensing system is above ground and may be accessed by a user. Referring now to FIG. 6, an exploded view of the upper portion of the present invention is shown. This upper portion comprises an access riser, a secondary safety lid, the liquid dispensing reservoir, a lid and a cap. The liquid reservoir and secondary safety lid rest substantially within the volume defined by the riser and lid.

Still referring to FIG. 6, riser 58 is placed on a base (not shown) which will rest on a water tank. Riser 58 has a plurality of tabs 60 (only one complete and one partial of which are shown here) extending centrally inward to opening 66. Each tab 60 contains screw holes 64 (only one of which is shown here) therein. A plurality of screw holes 62 are also spaced equidistantly around the circumference of riser 58.

Secondary safety lid 68 having surface 70, aperture 72 in the center thereof and contains a plurality of recessed portions 74 within which includes screw holes 76 (only one of which is shown here). Secondary safety lid 68 rests on plurality of tabs 60 of riser 58 with screw holes 76 of secondary safety lid 68 in alignment with screw holes 64 of riser 58. Fasteners (not shown), such as screws, traverse the plurality of screw holes 76 of secondary safety lid 68 and the plurality of screw holes 64 on the plurality of tabs 60 of riser 58 to fasten secondary safety lid 68 to riser 58.

Liquid dispensing reservoir 26 sits on surface 70 of secondary safety lid 68. Tubing 54 is connected at one end to fitting 52 (e.g., barbed fitting) secured within aperture 42. Tubing continues across surface 46 along partial groove 44 to where tubing 54 may connect to another component (sensing pipe). Band 56 secures tubing 54 as tubing 54 comes down from fitting 52 to minimize and/or eliminate movement which may cause tubing 54 to be unattached to fitting 52, as shown in FIG. 6.

Lid 78 has aperture 82 in the center and a plurality of screw holes 80 spaced equidistantly around the circumference of lid 78. Cap 84 includes an extending portion 88 held therein by adjusting pin 86 on cap 84. Extending portion 88 is hollow to accommodate cap 38 of liquid dispensing reservoir 26 therein. Lid 78 rests on top of riser 58 with the plurality of screw holes 80 of lid 78 in alignment with plurality of screw holes 62 of riser 58. Fasteners (not shown), such as screws, traverse the plurality of screw holes 80 of lid 78 and the plurality of screw holes 62 of riser 58 to fasten lid 78 to riser 58.

Figure 7:
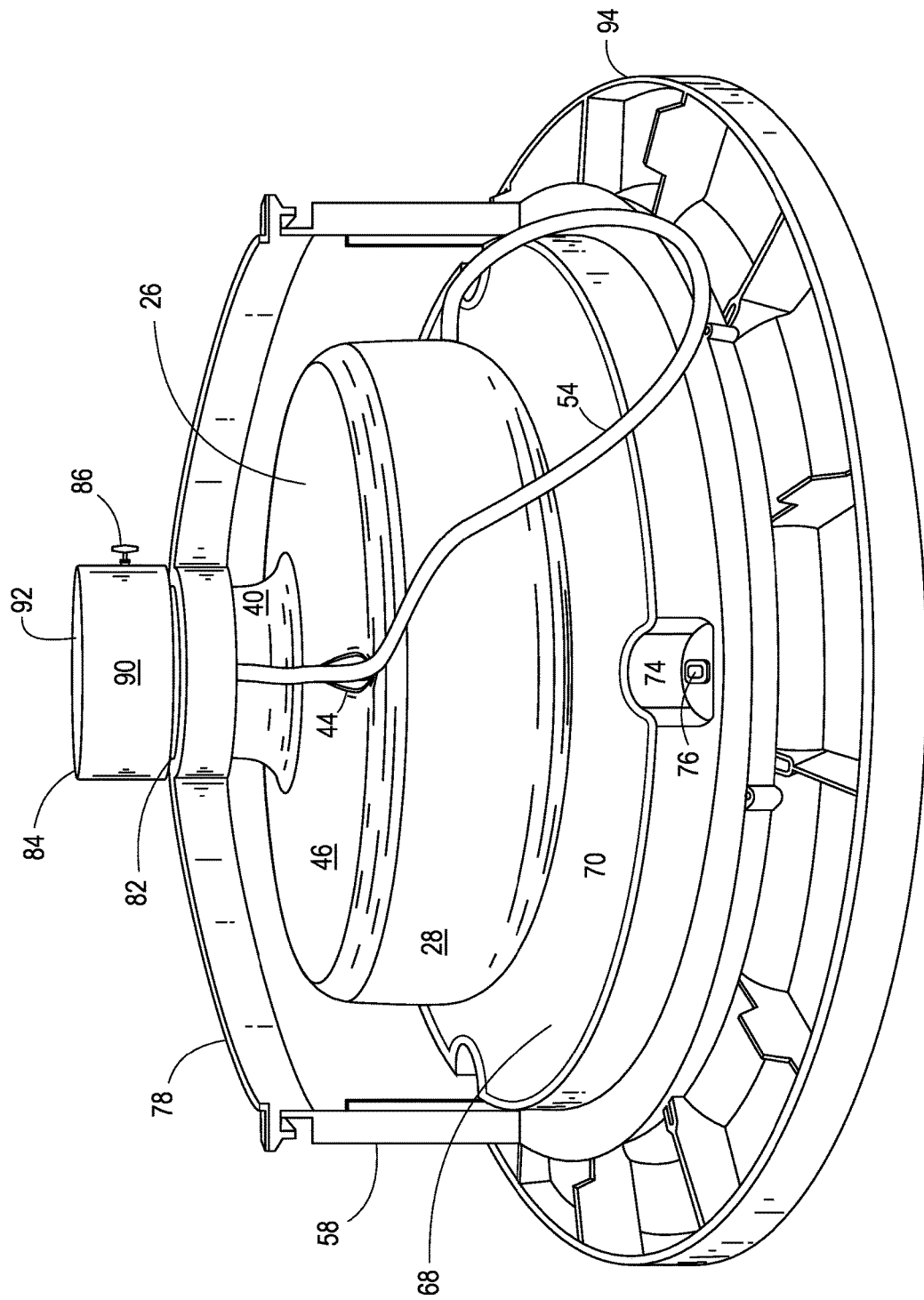
FIG. 7 is a partial sectional view of the disinfectant dispensing reservoir within the housing, with respect to FIG. 6.

FIG. 7 illustrates the various components of the upper portion of the dispensing system in FIG. 6 all resting on base 94. Similar to flat area 40, area 90 and top surface 92 may also be used for placement of embossed labeling, logo, data plate or other similar marking.

In one embodiment, liquid dispensing reservoir 26 may have handles (not shown) about the center of neck portion 30 to aid the user in lifting liquid dispensing reservoir 26 out during maintenance, repair or replacement of the reservoir.

The liquid dispensing reservoir may be used in conjunction with the liquid dispensing system of the present invention. Now referring to FIG. 8, dispensing system 96 of the present invention is shown within a pump tank 98. The upper portion of the dispensing system (previously described in reference to FIGS. 6 and 7) is attached to the top of tank 98. The present invention further comprises sensing pipe 100 connected at the top end to tubing 54 via connector 102. The opposite end of sensing pipe 100 is submerged under the liquid 108 within tank 98 and has open end 104. Brace 126 supports the vertical orientation of sensing pipe 100 within tank 98. Discharge pump 110 is submerged in liquid 108 within tank on one end and on the other end connects to discharge pipe 112. Braces 122 and 124 supports the vertical orientation of discharge pump 110 within tank 98.

An inlet line 109 allows for the entrance of liquid, e.g., untreated effluent. The present invention may also include fluid level indicator 114, such as a floating water level. Wiring 118 and 116 connect to and provide power to discharge pump 110 and fluid level indicator 114. Ties 128 may be used to secure wiring 118 and 116 (to, for example, discharge pump 110). Valve 120, rotatable about an opened position and a closed position, is located within discharge pipe 112.

Figure 8:
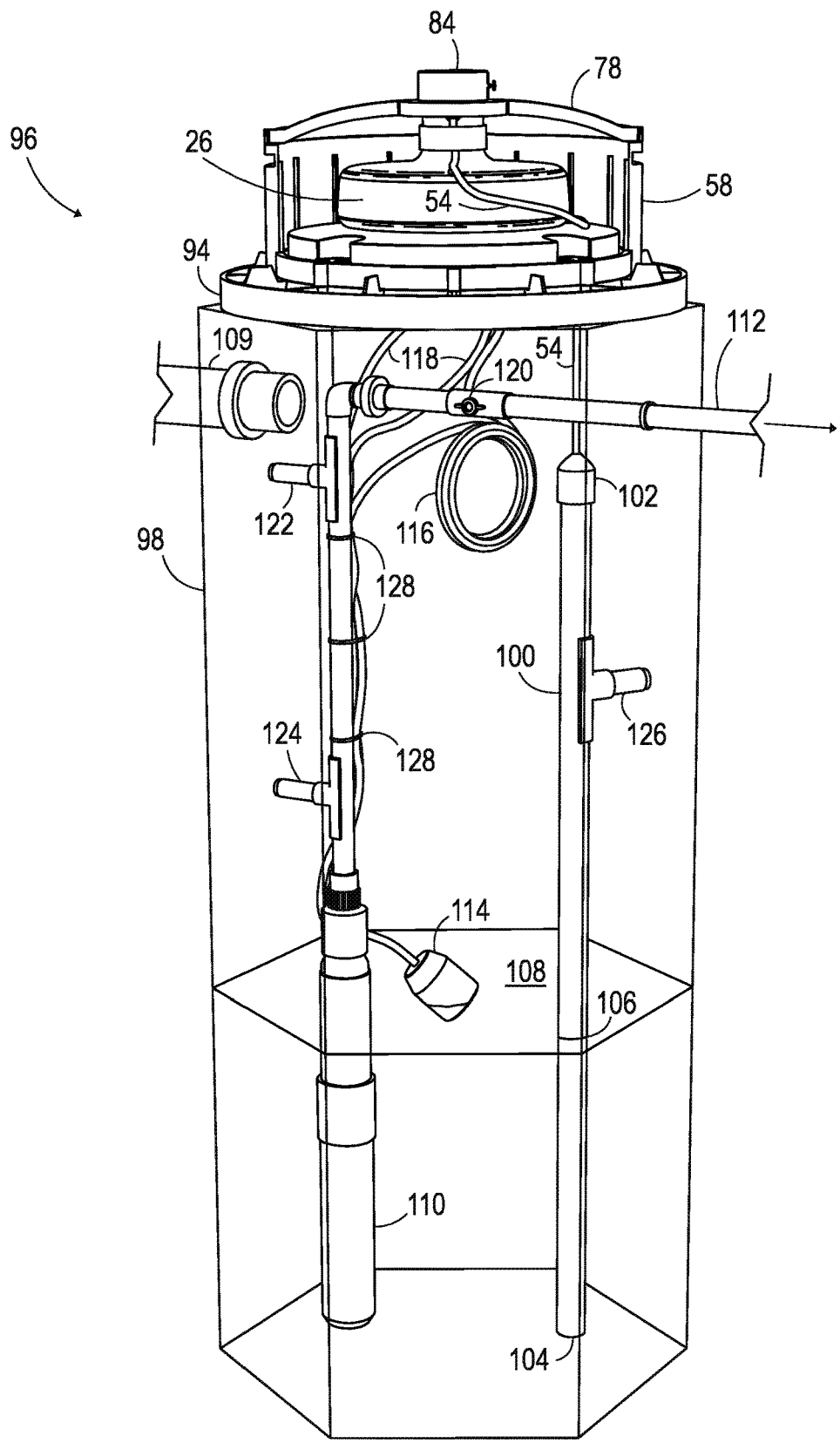
FIG. 8 shows a front view of the disinfectant dispensing system of the present invention showing the liquid within the sensing pipe at the same level as the liquid within a tank.
Figure 9:
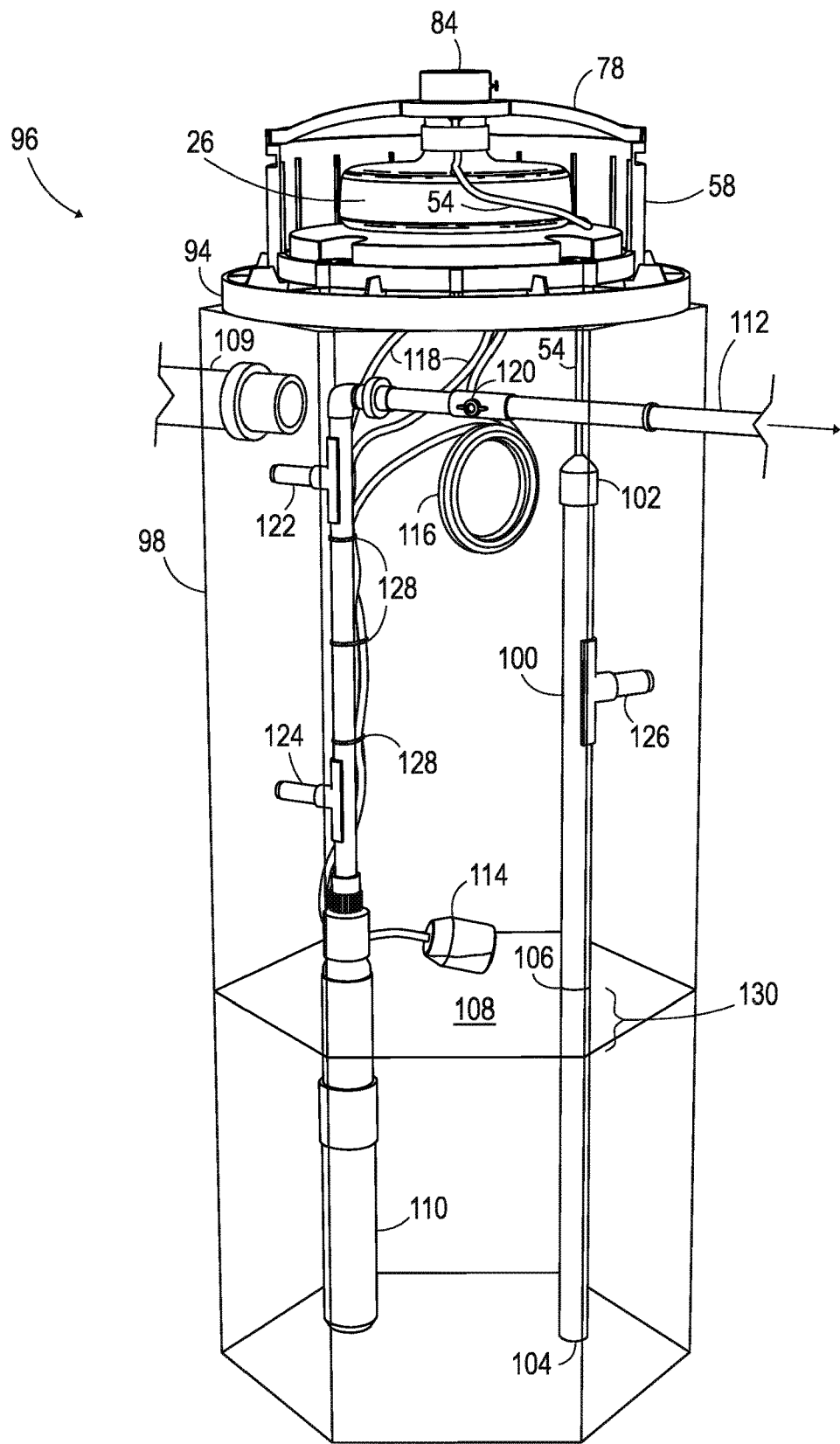
FIG. 9 depicts a front perspective view of an embodiment of the present invention showing the liquid beginning to rise within the sensing pipe.
Figure 10:
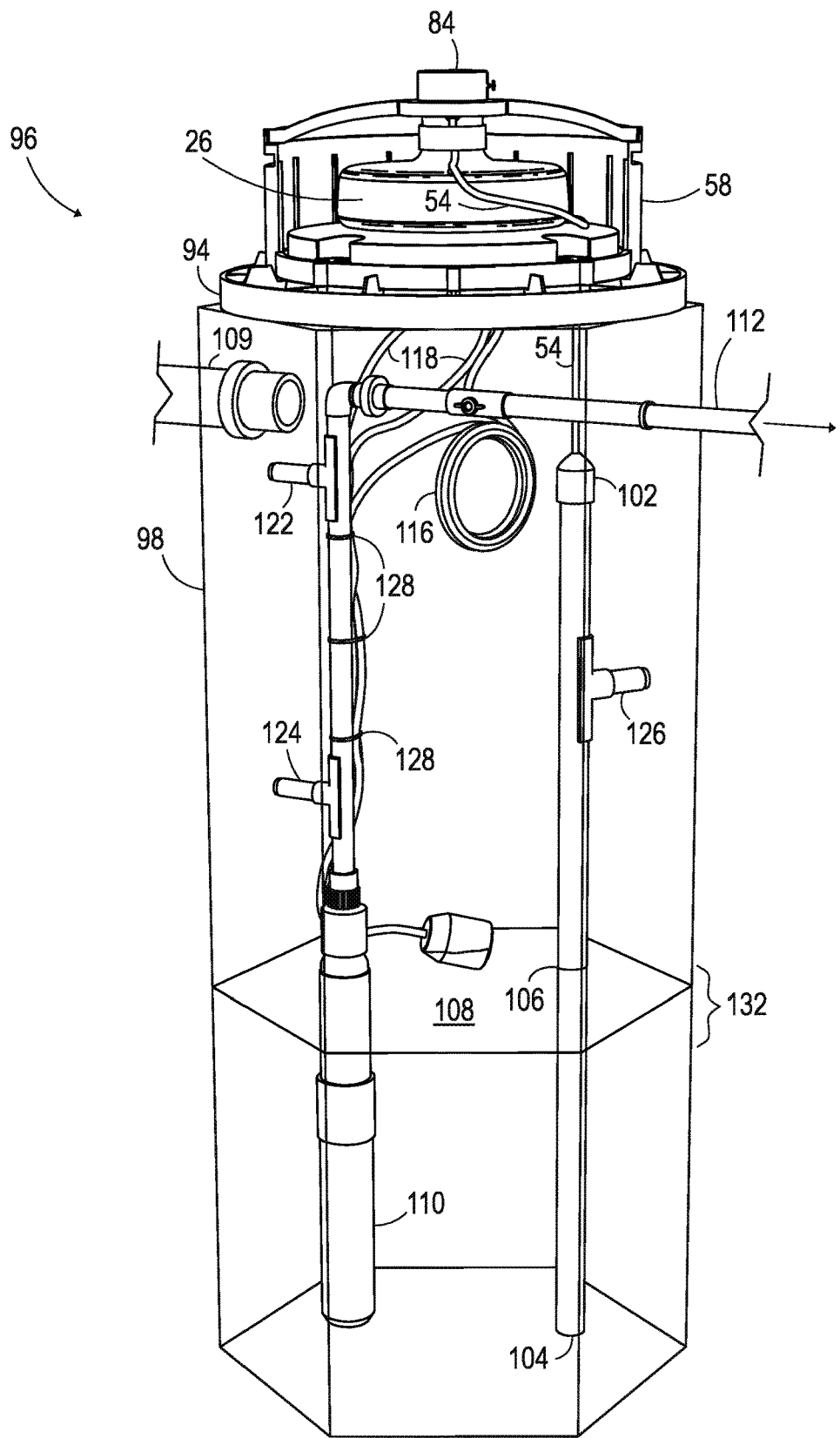
FIG. 10 shows a front perspective view of an embodiment of the present invention showing the water within the sensing pipe at an upper level.
Figure 11:
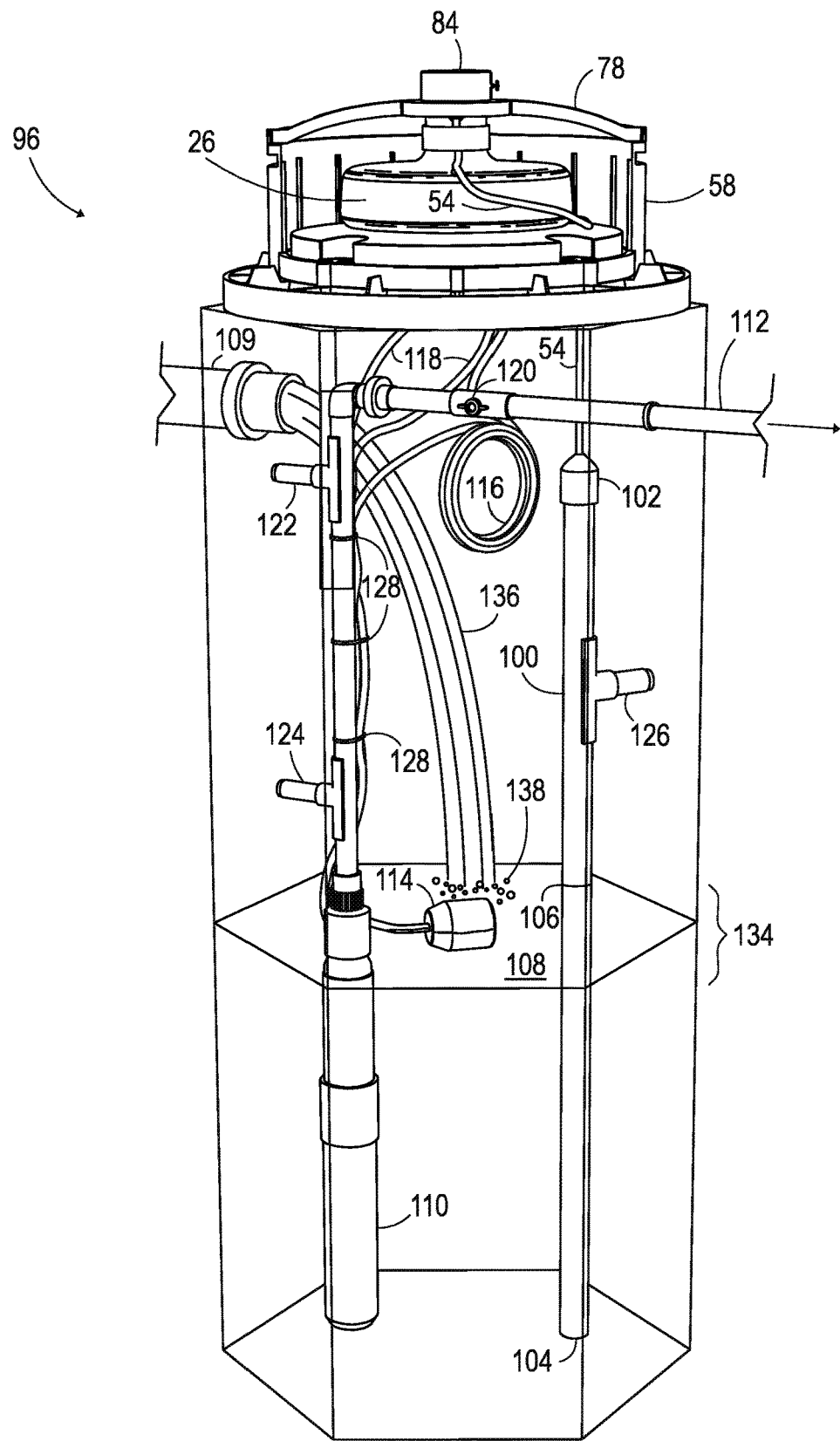
FIG. 11 is a front perspective view of an embodiment of the present invention showing the water within the sensing pipe at an upper level and the inlet water entering the tank.

Still referring to FIG. 8, riser rests on base 94 on top of tank 98. Riser 58 has a volume within capable of accommodating liquid dispensing reservoir 26. Aperture 27 on bottom 29 of liquid dispensing reservoir 26 is aligned with aperture 72 of secondary safety lid 68 and opening 66 of riser 58 to allow disinfectant from liquid dispensing reservoir 26 to drip into tank 98. Riser 58 is commercially available under the trademark TufTite® and has dimensions of 24" in diameter and 12" tall, though other dimensions may also be used and still remain within the contemplation of this present invention.

Referring still to FIG. 8, tubing 54 is connected to liquid dispensing reservoir 26 on one end and connected to sensing pipe 100 on the other end. The tubing may be ¼" vinyl tubing, though other comparable size tubing may be used and still remain within the contemplation of the present invention.

A single sensing pipe or tube 100 extends into the surface of the liquid 108 in tank 98 at one end and has an opening 104 therein. The other end of sensing tube 100 extends upwards towards riser 58. Sensing pipe 100 may be flexible or rigid, transparent or opaque. Sensing pipe 100 may be connected to additional tubing, e.g., vinyl tubing, to facilitate fluid communication with the liquid dispensing reservoir. It is to be understood that air may be considered a fluid in the present invention.

Inlet line 109 allows fluid, e.g., non-disinfected fluid such as liquid waste effluent, to enter into and fill tank 98. Discharge line or pipe 112 is used to discharge disinfected fluid from effluent pump 110 in tank 98 and communicated to a sprinkler or drain field. Discharge pump 110 is used to pump out the disinfected fluid through discharge line or pipe 112. A fluid level indicator 114, such as a floating water level, is used to determine the fluid level 108 within tank 98, as shown in FIG. 8 (see also, e.g., FIGS. 9, 10, 11 and 14). The liquid disinfectant used to disinfect the non-disinfected fluid, such as liquid waste effluent entering the tank, may be liquid chlorine (i.e., bleach), hydrogen peroxide, EDTA, or other liquid with similar disinfecting properties.

Referring now to FIGS. 8-11, the present invention in use is described. Referring to FIG. 8, prior to use, liquid 108 within sensing pipe 100 is at the same level 106 as the liquid contents within pump tank 98. Cap 84 of lid 78 is removed. Cap 38 (see, e.g., FIG. 6) of liquid dispensing reservoir 26 is then removed and liquid dispensing reservoir 26 is filled up with the appropriate liquid disinfectant. This would be approximately 3 gallons of a liquid, though containers of other sizes may be also be used for the liquid dispensing reservoir and still remain within the contemplation of this present invention. As liquid dispensing reservoir 26 is being filled up, small amounts of liquid escapes from aperture 27 on bottom 29 of liquid dispensing reservoir 26 and fall into pump tank 98.

The liquid dispensing reservoir of the present invention is a 3.5 gal tank. This size is optimal for most residential applications as the reservoir may be retrofitted snuggly within the risers already in the tanks of many consumers. However, residential users have a variety of sized tanks in use. The present invention may also accommodate those varied sized tanks by having the reservoir tank compatible for use in other sizes, including up to a 20 gallon tank, and still remain within the contemplation of the present invention.

Cap 38 is replaced back onto liquid dispensing reservoir 26 once the liquid contents are placed into liquid dispensing reservoir 26. Small amounts of liquid continue to fall into pump tank 98 from aperture 27 on bottom 29 of liquid dispensing reservoir 26 until the dispensing system of the present invention, which includes liquid dispensing reservoir 26, tubing 54 and submerged sensing pipe 100, reaches equilibrium in terms of pressure. However, replacing the lid creates a closed system and causes a vacuum to be created within sensing pipe 100. As the small amounts of liquid continue to fall into pump tank 98 from aperture 27 on bottom 29 of liquid dispensing reservoir 26, the vacuum created within the system causes (by pulling or suction)

liquid from pump tank 98 to be drawn and rise within sensing pipe 100, causing a rise in liquid within sensing pipe 100. See FIG. 9.

The liquid will continue to be drawn up to sensing pipe 100 until the level of liquid within sensing pipe 100 reaches an upper level, such upper level ranging from a few inches above the surface of the fluid 108 in the tank to approximately 12-14 inches or more. See, e.g., FIGS. 10 and 11. However, the sensing pipe fluid level can only rise to no more than the reservoir height. Such upper level reached coincides with the equalization of pressure in the system. Once the pressure in the system is equalized, no further liquid will fall into pump tank 98 from aperture 27 on bottom 29 of liquid dispensing reservoir 26.

The only time equalization must occur is when cap 38 of liquid dispensing reservoir 26 is removed for refilling. This occurs when liquid dispensing reservoir 26 has probably been out of liquid (e.g., bleach) for a while.

Equilibrium may also be reached with the level of liquid within sensing pipe 100 at approximately 6.5 inches. See FIG. 10 (showing an upper level 132 of approximately 6.5" above the surface of fluid 108 in tank 98). This equates to approximately ½ inch of vacuum.

Once equilibrium is reached and the level of liquid within sensing pipe 100 stops rising, the fill hose 109 is turned on. See FIG. 11.

As the fill hose 109 fills pump tank 98 with liquid 136, liquid 108 in pump tank 98 rises. As liquid 108 in pump tank 98 rises, column of liquid 134 within sensing pipe 100 also rises an equal distance, maintaining the same distance above the level of liquid 108 in pump tank 98 as when equilibrium was reached. In the example provided, this would be approximately 6.5 inches. Compare FIG. 9 with FIG. 10 (each depicting same level of column of liquid within sensing pipe at different levels of liquid within the pump tank). The system is still locked, but the volume of air above the water column within sensing pipe 100 controls the vacuum lock.

Figure 13:
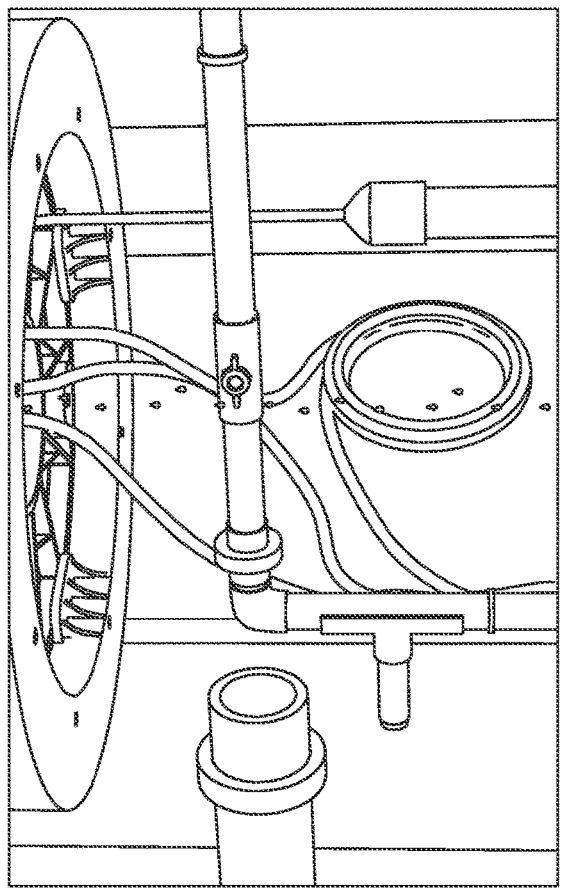
FIG. 13 shows a close up view of the disinfectant from the disinfectant dispensing reservoir dripping into the tank.
Figure 12:
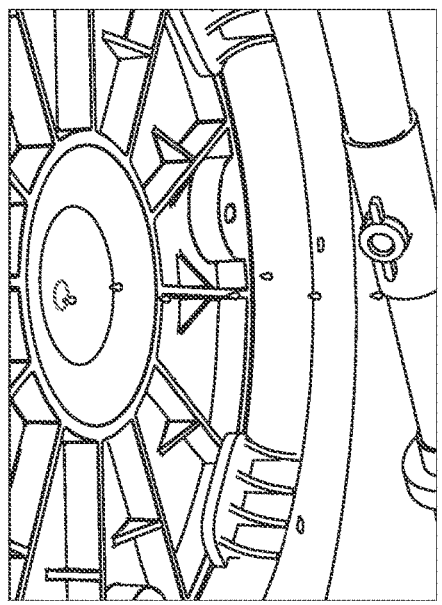
FIG. 12 is a front view of an embodiment of the present invention showing the water within the sensing pipe at an upper level and the inlet water entering the tank while the water within the tank continues to rise and the disinfectant from the liquid reservoir continuing to drip into the tank.

As the liquid level within sensing pipe 100 rises, fluid/dosing leaks out of the bottom of the liquid reservoir. It is the volume of air above the water column within sensing pipe 98 that is in fluid connection with the liquid dispensing reservoir 26 that "pushes" further dosing to occur via aperture 27 at bottom 29 of liquid dispensing reservoir 26. See, e.g., FIGS. 12 and 13 (depicting the rising column of water within the sensing pipe and the dosing shown as drops that take place).

Turning off fill hose 109 prevents further outside liquid to being introduced into pump tank 98. Also, as liquid no longer is rising within tank 98, the column of liquid within sensing pipe 100 also does not rise, but remains the same distance above the level of the liquid in pump tank 98 as when fill hose 109 was on, e.g., 6.5 inches. See FIG. 14.

The column of liquid within sensing pipe 100 remains the same distance above the level of the liquid in pump tank 98 throughout the process of filling and emptying pump tank 98 with liquid (with the level of liquid within the tank rising and falling), thereby controlling the dosing rate and amount of dosing that occurs.

Figure 14:
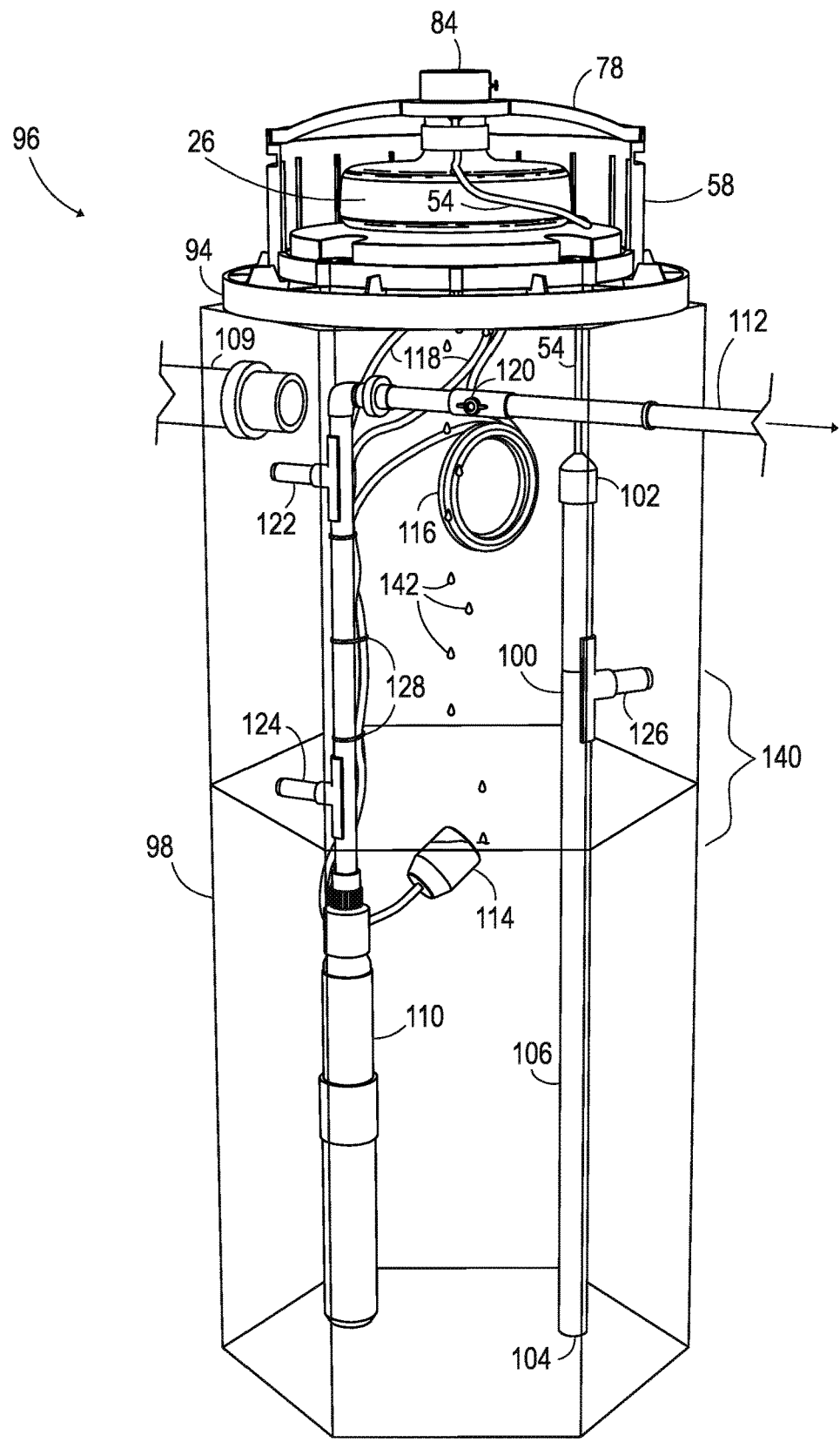
FIG. 14 is a front view of an embodiment of the present invention showing the water within the sensing pipe at an upper level, the inlet water no longer entering the tank and the height (or length) of the water within the sensing pipe at a constant height (or length) above the surface of the tank water.

Referring now to FIG. 14, once the liquid 108 in pump tank 98 has been disinfected, a pathway from tank 98 to an area remote from the tank is opened. Discharge pump 110 within tank 98 is then turned on via a switch or other similar means to pump out the now disinfected liquid via the outlet hose 112 to a sprinkler system or drain field. This is accomplished by turning ball valve 120 into an open position to open the pathway of the liquid within pump tank 98 into outlet hose 112 and out to the sprinkler or drain field, as shown in FIG. 14.

As the level of the liquid within the pump tank falls, so too does the level of the column of liquid within sensing pipe 100 which maintains the same distance above the level of the liquid in pump tank 98.

FIGS. 8-14 illustrate the functionality and progression of the dispensing system of the present invention, beginning with the liquid within sensing pipe 100 at the same level as the liquid level in tank 98 and gradually increasing to an upper level, reaching equilibrium and causing pressure to build within liquid dispensing reservoir 26. Thereafter, effluent 136 is introduced into tank 98. Dispensing of disinfectant occurs from aperture 27 on bottom 29 of liquid dispensing reservoir 26 forced out by pressure.

Figure 15:
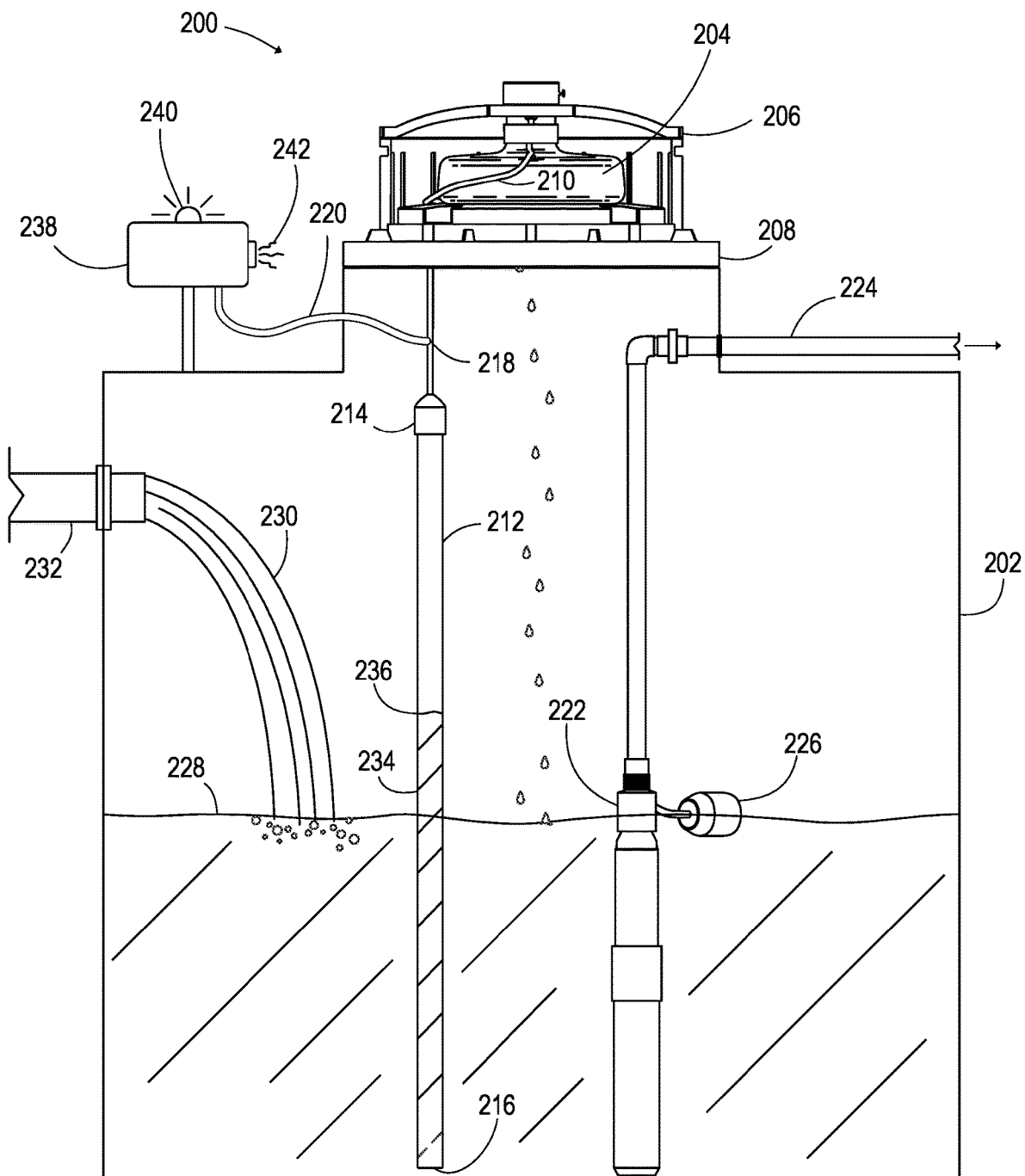
FIG. 15 depicts an embodiment of the present invention having alarms.

FIG. 15 depicts the integration of the present invention in an alternative embodiment 200 with liquid dispensing reservoir 204 having discharge pump 222, inlet pipe 232 and outlet or discharge pipe 224. Liquid dispensing reservoir 204 is shown within a partial cross section of riser 206 such that only a side view of the neck and bottom portion of the liquid dispensing reservoir is exposed. Riser 206 sits on tank 202.

Liquid dispensing reservoir 204 is in fluid communication via tubing 210 with sensing pipe 212 extending into liquid effluent 228 in tank 202. Visual alarm 240 and audible alarm 242 are integrated within an alarm assembly 238 with this embodiment of the present invention. Effluent 230 flows into and fills tank 202 from inlet pipe 232.

Still referring to FIG. 15, a "T" barbed fitting 218 is located inline of tubing 210 between reservoir 204 and sensing pipe 212. Fluid or lack of fluid, e.g., air, is communicated to alarm assembly 238 via tubing 220. Alarm assembly 238 may measure pressure, such that if a predetermined range is not maintained, such outside parameter may cause visual alarm 240 or audible alarm 242 or both to activate and alert the user.

The dispensing system of the present invention should generally be installed by a professional licensed by the appropriate licensing body or by a trained installer. To install, the user locates the aerobic system holding/pump tank and removes the access lid mounting screws and then removes the access lid. The user then installs the vertical sensing pipe into the holding/pump tank, ensuring that the sensing pipe is resting on the bottom of the holding/pump tank. The user then cuts the sensing pipe off below the top of the holding/pump tank lid, and secures the sensing pipe such that the sensing pipe remains in a vertical position in the holding/pump tank.

Using polyvinyl chloride (PVC) cleaner and PVC glue, the user then attaches the barb fitting adapter (supplied on the end of the vinyl tubing of the liquid dispensing reservoir) to the sensing pipe. The user then places the liquid dispensing reservoir inside the holding tank access riser. The liquid dispensing reservoir rests on the secondary safety lid inside the holding tank access riser. If the holding/pump tank access riser does not have a secondary safety lid, the user replaces the holding/pump tank access riser with a new access riser that accommodates the secondary safety lid to code.

Next, the user drills a 4.25 inch hole in the center of the holding/pump tank access lid. The hole allows the fill lid to be accessed without having to reopen the holding/pump tank lid. Next, the user then re-installs the holding/pump tank access lid and replaces the mounting and safety screws.

The user then opens the liquid dispensing reservoir gasketed fill lid and fills the tank with liquid disinfectant, such as 6%-10% sodium hypochlorite (household bleach). Once filled, the gasketed fill lid is replaced ensuring a firm secure seal. If the fill lid is not tightened securely, a vacuum will not form and the liquid dispensing reservoir will empty sodium hypochlorite contents into the holding/pump tank prematurely.

In use, the reservoir fill cap (gasketed) is removed from the reservoir. The reservoir fill cap is threaded and is rotated counterclockwise until the reservoir fill cap separates from the corresponding neck portion of the reservoir. The reservoir is then filled with several gallons, e.g., 3 gallons of disinfectant such as bleach or chlorine. The reservoir fill cap is then threaded screwed back on. An aperture is on the bottom side of the liquid dispensing reservoir. Bottom side view of 1/16" hole in reservoir in riser. As the reservoir drips out chlorine from the small hole in the bottom of the reservoir, it pulls a vacuum on the reservoir. That vacuum is transferred to the sensing pipe via the flexible tubing. When the water column is lifted high enough in the sensing pipe, the reservoir can no longer drip because of the "vacuum lock." This occurs at about 1" Hg. However, this can vary.

After this balancing process has been achieved, the reservoir and sensing pipe are "locked and loaded" and can stay this way indefinitely, i.e., reservoir is full of chlorine (chemical). There is a small hole in the bottom of the reservoir that will not leak/drip because of the vacuum. Water column in the sensing pipe is higher than the effluent in the tank.

Now, when water/effluent is added to the pump tank, the water column in the sensing pipe will stay the same height above the outside effluent level as the pump tank contents rise. Whether it is a half inch or several feet, the sensing pipe water column always stays higher (until reservoir runs out of bleach). So, as the pump tank contents rise, it is the column of air in the sensing pipe that controls the amount of chlorine desired to be released.

As the water level in the pump tank drops (i.e., water is pumped out to the sprinklers etc.), the water column in the sensing pipe follows the water level in the pump tank down. As the pump tank and sensing pipe levels follow each other down, atmospheric air enters the small hole in the chlorine storage reservoir. It is actually drawn in to the reservoir because the vacuum has increased above the level needed to achieve the initial vacuum balance.

In an alternative embodiment, a vacuum over electric switch (not shown) inline may be installed between the liquid dispensing reservoir 26 and sensing pipe 100. Once liquid dispensing reservoir 26 is filled and goes under a vacuum, the system will stay under a vacuum until liquid dispensing reservoir 26 runs out of liquid (e.g., bleach) or possibly tubing 54 gets cut or damaged. With the option of an alarm, this electric switch will detect a vacuum loss. This vacuum switch is low cost and does not come into contact with the liquid, e.g., chlorine. In addition, the vacuum switch may be remote mounted far away from the liquid reservoir connected via vacuum tubing, as shown in FIG. 15.

The range of the adjustable vacuum switch is as low as 0.10 inches of Hg. The reservoir and sensing pipe can balance/vacuum lock as low as 0.5 inches of Hg upwards to at least 1 inch Hg. The adjustable vacuum switch may be installed inside the existing aerobic system control panel. There is already a low pressure switch installed for the aerator alarm circuit or assembly 238 consisting of an audible alarm 242 and visual alarm 240, as shown in FIG. 15. The alarm switch of the present invention can parallel that existing circuit in the existing control box 238, or a separate circuit and/or a separate alarm panel.

In an alternative embodiment, and as shown in FIG. 15, an alarm or plurality of alarms may be incorporated with the present invention. In the past, colored lights (e.g., red, yellow and green) have been used in conjunction with audible alarms to signal aerobic aeration malfunction (yellow), pump tank high water alarms (red) and low chlorine levels (green). Perhaps it may have been time consuming to discuss issues with a customer and ask the customer what color the light was that was being displayed. Currently all alarms are red and known in the industry as "one light control panels". However, with these one light alarms it has become extremely difficult, if at all possible to ascertain what part of the aerobic system has failed.

Aerobic systems require physical service by a qualified technician. For example, each aerobic system in Texas has to be physically serviced once every 4 months. Service companies have 24 hours to respond to trouble calls. Some of the service companies have 4000+ annual maintenance contracts which equates to thousands of phone calls.

The present invention further comprises a low cost 120V flasher (e.g., visual alarm). This low level/malfunction alarm allows for rapid diagnosis over the phone when discussing an issue with the end user, e.g., customer.

By installing a flasher in line with the low vacuum switch circuit, the chlorinator low level alarm circuit will flash. So the customer, service company, health department, etc. . . . will be able to identify the malfunction within a combined alarm system. The electrical components (vac switch/flasher) of the present invention will install inside the existing control panel circuitry easily, as for example, a "plug and play" component. Such method for an alarm circuit has not been utilized in the disinfection industry.

Other types of alarms that may be incorporated with the present invention include kind of alarm audible (siren), visual (lights) and also notifications sent to a smart device, such as an iPad, smart phone or the like.

The dispensing system of the present invention functions under normal use or intermittent periods of use. If periods of non-use exceed six (6) months, the liquid dispensing reservoir should be drained and refilled with liquid disinfectant, e.g., 6-10% sodium hypochlorite.

The present invention has application in water and wastewater treatment systems as well as above-water storage tanks, such as rainwater collection storage tank disinfection systems, and generally for any water level that may fluctuate within a tank. It may utilize any kind of disinfectant, including chemicals such as chlorine, Ethylenediaminetetraacetic acid (EDTA), peracetic acid or peroxyacetic acid (PAA), hydrogen peroxide ($H_2O_2$) and the like, to accommodate and be commensurate with a variety of regulatory standards.

The various embodiments described herein may be used singularly or in conjunction with other similar devices. The present disclosure includes preferred or illustrative embodiments of specifically described apparatuses, assemblies, and systems. Alternative embodiments of such apparatuses, assemblies, and systems can be used in carrying out the invention as described herein. Other aspects and advantages of the present invention may be obtained from a study of this disclosure and the drawings.

I claim:

1. A method of installation of a vacuumed controlled level sensing liquid dispensing system, said method comprising steps of:
   locating a holding tank having a lid and a riser;
   removing said lid and said riser from said holding tank;
   placing a sensing pipe into said holding tank;
   configuring said sensing pipe to be within said holding tank;
   securing said sensing pipe to said holding tank;
   attaching a fitting to a top end of said sensing pipe;
   replacing said riser of said holding tank;
   placing a liquid dispensing reservoir within said riser of said holding tank;
   connecting a first end of a tubing to said fitting and a second end of said tubing to said liquid dispensing reservoir;
   drilling an aperture in a center of said lid of said holding tank;
   replacing said lid of said holding tank; and
   wherein said installation is performed by a trained installer.

2. A method for dispensing of liquid disinfectant using a vacuumed controlled level sensing liquid dispensing system for disinfecting a body of effluent, said method comprising steps of:
   removing a cap from a reservoir;
   filling said reservoir with a disinfectant;
   replacing said cap onto said reservoir;
   establishing equilibrium of pressure within said vacuumed controlled level sensing liquid dispensing system;
   adding liquid to be treated into a holding tank;
   dosing said liquid to be treated within said holding tank with said disinfectant;
   opening a pathway from said holding tank to a remote location; and
   pumping out said liquid now disinfected from said holding tank to said remote location.

* * * * *